US011439453B2

(12) United States Patent
Winkelman et al.

(10) Patent No.: US 11,439,453 B2
(45) Date of Patent: Sep. 13, 2022

(54) SYSTEMS AND METHODS FOR TATTOO REMOVAL USING COLD PLASMA

(71) Applicant: Clear Intradermal Technologies, Inc., New York, NY (US)

(72) Inventors: James W. Winkelman, Chestnut Hill, MA (US); Martin E. Schmieg, Delray Beach, FL (US)

(73) Assignee: Clear Intradermal Technologies, Inc., New York, NY (US)

( * ) Notice: Subject to any disclaimer, the term of this patent is extended or adjusted under 35 U.S.C. 154(b) by 0 days.

(21) Appl. No.: 16/902,767

(22) Filed: Jun. 16, 2020

(65) Prior Publication Data

US 2020/0305950 A1 Oct. 1, 2020

Related U.S. Application Data

(62) Division of application No. 15/155,750, filed on May 16, 2016, now Pat. No. 10,716,611.

(Continued)

(51) Int. Cl.
*A61B 18/14* (2006.01)
*A61B 18/04* (2006.01)
(Continued)

(52) U.S. Cl.
CPC ........ *A61B 18/042* (2013.01); *A61B 18/1477* (2013.01); *A61K 8/19* (2013.01);
(Continued)

(58) Field of Classification Search
CPC ........ A61B 2017/00769; A61B 18/042; A61B 2018/00583; A61B 18/1477;
(Continued)

(56) References Cited

U.S. PATENT DOCUMENTS 4,634,420 A 1/1987 Spinosa et al.
5,217,455 A 6/1993 Tan
(Continued)

FOREIGN PATENT DOCUMENTS

DE 112009000734 T5 4/2011
DE 102011001416 A1 9/2012
(Continued)

OTHER PUBLICATIONS

U.S. Appl. No. 16/711,545, filed Dec. 12, 2019, Winkelman, et al.
(Continued)

*Primary Examiner* — Joanne M Hoffman
*Assistant Examiner* — Sean W Collins
(74) *Attorney, Agent, or Firm* — Potomac Law Group, PLLC; Reza Mollaaghababa

(57) ABSTRACT

A method and system for tattoo removal from a subject by exposing tattoo ink particles trapped within the dermis to a cold plasma is described herein. The tattoo removal method and system can be used to remove the tattoo from the skin of the subject being treated. In addition, the method and system described allows for the extraction of the tattoo ink particles, which may have toxic properties, from the subject's body.

18 Claims, 4 Drawing Sheets

Related U.S. Application Data

(60) Provisional application No. 62/162,180, filed on May 15, 2015.

(51) Int. Cl.
*A61K 8/19* (2006.01)
*A61K 8/22* (2006.01)
*A61Q 1/14* (2006.01)
*A61B 18/00* (2006.01)
*A61B 17/00* (2006.01)
*A61N 1/44* (2006.01)
*H05H 1/46* (2006.01)

(52) U.S. Cl.
CPC ............... *A61K 8/22* (2013.01); *A61Q 1/145* (2013.01); *A61B 2017/00769* (2013.01); *A61B 2017/00973* (2013.01); *A61B 2018/0016* (2013.01); *A61B 2018/0047* (2013.01); *A61B 2018/00196* (2013.01); *A61B 2018/00583* (2013.01); *A61B 2018/00916* (2013.01); *A61B 2218/002* (2013.01); *A61B 2218/007* (2013.01); *A61N 1/44* (2013.01); *H05H 1/466* (2021.05)

(58) Field of Classification Search
CPC .... A61B 2017/00973; A61B 2218/007; A61B 2218/002; A61B 2018/00916; A61B 2018/0047; A61B 2018/0016; A61B 2018/00196; A61Q 1/145; A61K 8/22; A61K 8/19; H05H 1/466
See application file for complete search history.

(56) References Cited

U.S. PATENT DOCUMENTS

| | | | |
|---|---|---|---|
| 5,873,849 A | 2/1999 | Bernard | |
| 6,053,172 A | 4/2000 | Hovda et al. | |
| 6,394,956 B1 | 5/2002 | Chandrasekaran et al. | |
| 6,607,513 B1 | 8/2003 | Down et al. | |
| 6,770,070 B1 * | 8/2004 | Balbierz | A61B 10/04 600/566 |
| 6,896,672 B1 | 5/2005 | Eggers et al. | |
| 7,330,755 B2 | 2/2008 | Viol et al. | |
| 7,402,435 B2 | 7/2008 | Miyoshi et al. | |
| 7,608,839 B2 | 10/2009 | Coulombe et al. | |
| 7,633,231 B2 | 12/2009 | Watson | |
| 7,683,342 B2 | 3/2010 | Morfill et al. | |
| 7,923,251 B2 | 4/2011 | Vankov et al. | |
| 8,005,548 B2 | 8/2011 | Watson | |
| 8,103,340 B2 | 1/2012 | Viol | |
| 8,283,171 B2 | 10/2012 | Vankov et al. | |
| 8,377,388 B2 | 2/2013 | Konesky | |
| 8,388,618 B2 | 3/2013 | Fridman et al. | |
| 8,455,228 B2 | 6/2013 | Jaroszeski et al. | |
| 8,460,283 B1 | 6/2013 | Laroussi et al. | |
| 8,521,274 B2 | 8/2013 | Gutsol et al. | |
| 8,557,187 B2 | 10/2013 | Ehlbeck et al. | |
| 8,725,248 B2 | 5/2014 | Gutsol et al. | |
| 8,802,022 B2 | 8/2014 | Konesky | |
| 8,810,134 B2 | 8/2014 | Watson | |
| 8,828,326 B2 | 9/2014 | Holbeche | |
| 8,894,644 B2 | 11/2014 | Stieber et al. | |
| 8,900,521 B2 | 12/2014 | Hancock | |
| 8,906,659 B2 | 12/2014 | Clyne et al. | |
| 8,926,920 B2 | 1/2015 | Morfill et al. | |
| 8,928,230 B2 | 1/2015 | Watson et al. | |
| 8,957,572 B2 | 2/2015 | Eden et al. | |
| 8,992,518 B2 | 3/2015 | Fridman et al. | |
| 8,994,271 B2 | 3/2015 | Kindel et al. | |
| 9,005,188 B2 | 4/2015 | Wandke et al. | |
| 9,006,976 B2 | 4/2015 | Watson et al. | |
| 9,038,645 B2 | 5/2015 | Wandke et al. | |
| 9,072,157 B2 | 6/2015 | Holbeche et al. | |
| 9,192,776 B2 | 11/2015 | Hummel et al. | |
| 9,226,790 B2 | 1/2016 | Zemel et al. | |
| 9,236,227 B2 | 1/2016 | Watson et al. | |
| 9,257,264 B2 | 2/2016 | Hummel et al. | |
| 9,287,094 B2 | 3/2016 | Trutwig et al. | |
| 9,295,535 B2 | 3/2016 | Holbeche et al. | |
| 9,308,285 B2 | 4/2016 | Hancock et al. | |
| 9,330,890 B2 | 5/2016 | Busse et al. | |
| 9,339,783 B2 | 5/2016 | Fridman et al. | |
| 9,345,120 B2 | 5/2016 | Wandke et al. | |
| 9,351,790 B2 | 5/2016 | Zemel et al. | |
| 9,384,947 B2 | 7/2016 | Watson et al. | |
| 9,387,369 B2 | 7/2016 | Yamamoto | |
| 9,418,820 B2 | 8/2016 | Watson et al. | |
| 9,437,401 B2 | 9/2016 | Watson et al. | |
| 9,440,057 B2 | 9/2016 | Jacofsky et al. | |
| 9,472,382 B2 | 10/2016 | Jacofsky | |
| 9,498,637 B2 | 11/2016 | Sanders et al. | |
| 9,511,240 B2 | 12/2016 | Dobrynin et al. | |
| 9,521,736 B2 | 12/2016 | Jacofsky et al. | |
| 9,538,630 B2 | 1/2017 | Watson | |
| 9,558,918 B2 | 1/2017 | Watson et al. | |
| 9,570,273 B2 | 2/2017 | Watson et al. | |
| 9,601,317 B2 | 3/2017 | Konesky | |
| 2001/0029373 A1 | 10/2001 | Baker et al. | |
| 2003/0125727 A1 | 7/2003 | Truckai et al. | |
| 2006/0058238 A1 | 3/2006 | Laurent-Applegate et al. | |
| 2007/0027446 A1 | 2/2007 | Goble | |
| 2007/0078448 A1 | 4/2007 | Lipman | |
| 2008/0221548 A1 | 9/2008 | Danenberg et al. | |
| 2009/0112205 A1 | 4/2009 | McGill et al. | |
| 2010/0107744 A1 | 5/2010 | Fukuda et al. | |
| 2010/0228182 A1 | 9/2010 | Clark, III et al. | |
| 2010/0247687 A1 | 9/2010 | Arnold-Ronish | |
| 2010/0249768 A1 | 9/2010 | Avramenko | |
| 2010/0262135 A1 | 10/2010 | Berube | |
| 2011/0022043 A1 | 1/2011 | Wandke et al. | |
| 2011/0171188 A1 | 7/2011 | Morfill et al. | |
| 2011/0301412 A1 | 12/2011 | Cho | |
| 2012/0046597 A1 | 2/2012 | Morfill et al. | |
| 2012/0046602 A1 | 2/2012 | Morfill et al. | |
| 2012/0046658 A1 | 2/2012 | Kreindel | |
| 2012/0064016 A1 | 3/2012 | Lloyd et al. | |
| 2012/0080412 A1 | 4/2012 | Holbeche et al. | |
| 2012/0107761 A1 | 5/2012 | Holbeche et al. | |
| 2012/0107896 A1 | 5/2012 | Wandke et al. | |
| 2012/0288934 A1 | 11/2012 | Weltmann et al. | |
| 2013/0026137 A1 | 1/2013 | Kindel et al. | |
| 2013/0040542 A1 | 2/2013 | Schwappach et al. | |
| 2013/0147340 A1 | 6/2013 | Holbeche | |
| 2013/0345620 A1 | 12/2013 | Zemel et al. | |
| 2014/0188037 A1 | 7/2014 | Jacofsky et al. | |
| 2014/0188071 A1 | 7/2014 | Jacofsky et al. | |
| 2014/0188097 A1 | 7/2014 | Watson et al. | |
| 2014/0188195 A1 | 7/2014 | Jacofsky et al. | |
| 2014/0200506 A1 | 7/2014 | Zemel et al. | |
| 2014/0207053 A1 | 7/2014 | Morfill et al. | |
| 2014/0257276 A1 | 9/2014 | Sartor | |
| 2014/0341786 A1 | 11/2014 | Konesky | |
| 2014/0378892 A1 * | 12/2014 | Keidar | A61B 18/042 604/23 |
| 2015/0004248 A1 | 1/2015 | Morfill et al. | |
| 2015/0071099 A1 | 3/2015 | Yi et al. | |
| 2015/0088234 A1 | 3/2015 | Weltmann et al. | |
| 2015/0094647 A1 | 4/2015 | Kalghatgi et al. | |
| 2015/0112300 A1 | 4/2015 | Glowacki et al. | |
| 2015/0123711 A1 | 5/2015 | Mandela et al. | |
| 2015/0151135 A1 | 6/2015 | Kalghatgi et al. | |
| 2015/0157870 A1 | 6/2015 | Kalghatgi et al. | |
| 2015/0209595 A1 | 7/2015 | Kalghatgi et al. | |
| 2015/0340207 A1 | 11/2015 | Holbeche | |
| 2016/0045246 A1 | 2/2016 | Stieber et al. | |
| 2016/0089545 A1 | 3/2016 | Juluri et al. | |
| 2016/0100853 A1 * | 4/2016 | Hyde | A61B 90/361 600/309 |
| 2016/0106993 A1 | 4/2016 | Watson et al. | |
| 2016/0113701 A1 | 4/2016 | Zemel et al. | |
| 2016/0121134 A1 | 5/2016 | Kalghatgi et al. | |
| 2016/0166818 A1 | 6/2016 | Kalghatgi et al. | |

(56) References Cited

U.S. PATENT DOCUMENTS

| | | |
|---|---|---|
| 2016/0192961 A1 | 7/2016 | Ginggen et al. |
| 2016/0220670 A1 | 8/2016 | Kalghatgi et al. |
| 2016/0236002 A1 | 8/2016 | Dirk et al. |
| 2016/0242269 A1 | 8/2016 | Dirk et al. |
| 2016/0271411 A1 | 9/2016 | Hummel et al. |
| 2016/0271412 A1 | 9/2016 | Hummel et al. |
| 2016/0331436 A1 | 11/2016 | Holbeche |
| 2016/0331437 A1 | 11/2016 | Holbeche et al. |
| 2016/0331439 A1 | 11/2016 | Winkelman et al. |
| 2016/0331989 A1 | 11/2016 | Cho et al. |
| 2016/0338184 A1 | 11/2016 | Holbeche |
| 2016/0338755 A1 | 11/2016 | Holbeche et al. |
| 2016/0354614 A1 | 12/2016 | Watson et al. |
| 2016/0361558 A1 | 12/2016 | Jacofsky et al. |
| 2017/0246440 A1 | 8/2017 | Kalghatgi et al. |
| 2017/0246468 A1 | 8/2017 | Kalghatgi et al. |
| 2017/0326347 A1 | 11/2017 | Kalghatgi et al. |
| 2018/0103991 A1 | 4/2018 | Linhart et al. |
| 2018/0130646 A1 | 5/2018 | Louis |
| 2018/0311079 A1 | 11/2018 | Garibyan et al. |
| 2020/0197077 A1 | 6/2020 | Winkelman et al. |
| 2020/0197078 A1 | 6/2020 | Winkelman et al. |
| 2020/0352620 A1 | 11/2020 | Winkelman et al. |

FOREIGN PATENT DOCUMENTS

| | | |
|---|---|---|
| DE | 102013107448 B4 | 11/2016 |
| EP | 1638469 A2 | 3/2006 |
| EP | 1670369 A1 | 6/2006 |
| EP | 2016809 A2 | 1/2009 |
| EP | 1810626 B1 | 1/2012 |
| EP | 3051926 A1 | 8/2016 |
| FR | 983602 A | 6/1951 |
| JP | 2009507773 A | 2/2009 |
| JP | 2014212839 A | 11/2014 |
| JP | 6208968 B2 | 10/2017 |
| KR | 20150142162 A | 12/2015 |
| KR | 1020160121809 A | 10/2016 |
| RU | 2727147 C1 | 7/2020 |
| WO | 0064514 A1 | 11/2000 |
| WO | 0074767 A2 | 12/2000 |
| WO | 2001050963 A1 | 7/2001 |
| WO | 0236027 A2 | 5/2002 |
| WO | 2003096767 A1 | 11/2003 |
| WO | 2005020828 A1 | 3/2005 |
| WO | 2007015232 A1 | 2/2007 |
| WO | 2010107746 A1 | 9/2010 |
| WO | 2011/055368 A2 | 5/2011 |
| WO | 2011058301 A1 | 5/2011 |
| WO | 2011128620 A1 | 10/2011 |
| WO | 2012106735 A2 | 8/2012 |
| WO | 2012167089 A1 | 12/2012 |
| WO | 2014020584 A1 | 2/2014 |
| WO | 2015021434 A2 | 2/2015 |
| WO | 2016020407 A1 | 2/2016 |
| WO | 2016037599 A1 | 3/2016 |
| WO | 2016079742 A1 | 5/2016 |
| WO | 2016128873 A1 | 8/2016 |
| WO | 2016187132 A1 | 11/2016 |
| WO | 2016192986 A1 | 12/2016 |
| WO | 2016192997 A1 | 12/2016 |
| WO | 2017008781 A1 | 1/2017 |
| WO | 2017021585 A1 | 2/2017 |
| WO | 2020131544 A1 | 6/2020 |
| WO | 2020131545 A1 | 6/2020 |

OTHER PUBLICATIONS

U.S. Appl. No. 16/711,549, filed Dec. 12, 2019, Winkelman, et al.
U.S. Appl. No. 16/938,694, filed Jul. 24, 2020, Winkelman, et al.
Australin Examination Report, AU2016263428, dated Sep. 4, 2020, 5 pages.
Japanese Office Action, JP2018-511363, dated Dec. 22, 2020, 4 pages.
International Preliminary Report on Patentability, PCT/US2019/065873, dated Jul. 1, 2021, 9 Pages.
International Preliminary Report on Patentability, PCT/US2019/065876, dated Jul. 1, 2021, 10 Pages.
International Search Report and Written Opinion, PCT/US2021/042267 dated Oct. 29, 2021, 13 pages.
Choi, J-H. et al., "Treatment with low-temperature atmospheric pressure plasma enhances cutaneous delivery of Epidermal growth factor by regulating E-cadherin-medicated cell junctions," Arch Dermatol., vol. 306:635-643 (2014).
Colver, et al. "Tattoo Removal Using a Liquid Nitrogen Cryospray" Clinical and Experimental Dermatology, vol. 9, No. 1, Jul. 1, 1984, pp. 364-366.
Gucker, Plasma Discharges in Gas Bubbles in Liquid Water: Breakdown Mechanisms and Resultant Chemistry Ph.D. Thesis, University of Michigan (2015), 2 Pages.
Hamon, et al. Characterization of Plasma Generation in Bubbles With a Plasma Gun. 22nd International, 1 Page, (Year: 2018).
International Search Report and Written Opinion, PCT/US2016/032731, dated Aug. 1, 2016, 9 pages.
International Search Report and Written Opinion, PCT/US2017/019259 dated May 31, 2017, 14 pages.
International Search Report and Written Opinion, PCT/US2019/065873, dated Apr. 17, 2020, 15 pages.
International Search Report and Written Opinion, PCT/US2019/065876, dated Apr. 6, 2020, 16 pages.
Japanese Office Action, JP2018-511363, dated Mar. 17. 2020, 3 pages.
Sommers et al. Plasma Formation in Underwater Bubbles, Plasma Sources Science and Technology, vol. 23, No. 1 (2014), 5 Pages.
Huzaira M et al., "Magnetic Tattoos", Lasers in Surgery and Medicine, New York, NY, US, vol. 31, No. 2, Aug. 1, 2002 (Aug. 1, 2002), pp. 121-128.
International Search Report and Written Opinion, PCT/US2021/058746, dated Feb. 23, 2022, 16 pages.
Japanese Office Action for Japanese Application No. 2021-071986, dated Mar. 8, 2022.
Mexican First Office Action, MX/a/2020/013395, dated Mar. 10, 2022, 4 pages.
Bobrova et al., "Russian laser optician invents gentle way of removing tattoos", published Nov. 13, 2013, "https://www.rbth.com/economics/2013/11/13/russian_laser_optician_invents_gentle_way_of_removing_tattoos_30815".
Canadian Examination Report, CA2986031, dated May 30, 2022, 4 pages.
European Examination Report, EP16725994.4, dated May 16, 2022, 6 pages.

* cited by examiner

FRONT VIEW

SIDE VIEW

SYSTEMS AND METHODS FOR TATTOO REMOVAL USING COLD PLASMA

CROSS-REFERENCE TO RELATED APPLICATIONS

This application is a divisional of U.S. patent application Ser. No. 15/155,750, filed May 16, 2016, entitled "Systems and Methods for Tattoo Removal Using Cold Plasma," which claims the priority to U.S. Provisional Patent Application No. 62/162,180, filed May 15, 2015, entitled "Systems and Methods for Tattoo Removal Using Cold Plasma," the contents of which are incorporated by reference herein in its entirety.

FIELD

This present teachings are generally in the field of tattoo removal utilizing cold plasma-based systems and methods.

BACKGROUND

For many individuals, tattoos represent an important form of artistic self-expression. Other reasons for obtaining tattoos include permanent cosmetic applications and to cover scars or blemishes.

Permanent tattoos are created by piercing the skin with needles or similar instruments to mechanically deliver an ink, which includes small particles of pigments/dyes suspended in a carrier, into the dermis of an individual. The creation of a permanent tattoo requires the insertion/implantation of pigments, dyes, and/or chromophores which are not dissolvable and/or biodegradable. Following mechanical insertion of the ink particles and during the healing process, the majority of the ink particles, 70-80%, are engulfed by phagocytic skin cells (such as fibroblasts and macrophages) or retained in the extracellular matrix of the dermis and the remaining ink particles are found such that 10-15% of the ink particles lie flattened on collagen fibers and 5-10% of the ink particles lie attached on the serosal side of capillaries. Over time, the tattoo inks may migrate and descend deeper into the dermis, so the tattoos become blurred and duller.

Despite the wide acceptance and popularity of permanent tattoos, there is a significant demand for the removal of tattoos. Removal of tattoos, however, represents a complex process that most typically involves the use of high power lasers. The current state-of-the-art for tattoo removal is performed using a variety of lasers which induce degradation of the inks to achieve tattoo removal. The laser conditions require matching the laser frequencies to the particles according to their size, composition, color, and depth in the dermis. The laser is applied to the tattoo such that the pigments, dyes, and/or chromophores of the ink particles absorb the laser light and the laser pulses dissociate and degrade the pigments, dyes, and/or chromophores components of the ink particles into small(er) fragments. The fragmented ink components may become essentially colorless and small enough to be absorbed by the body and removed from the dermis. Nonetheless, laser-based removal of tattoos has several shortcomings. For example, lasers induce heating of the skin and can cause burns as well as other undesirable tissue damage which can cause some scarring or color variations that are likely to remain after healing. Current laser-based procedures for tattoo removal may therefore be somewhat ineffective at complete removal of tattoo inks, require multiple treatments at a high cost, cause pain, and can result in scarring, disfigurement, and depigmentation of the treated skin.

Therefore, it would be advantageous to provide a system and methods for tattoo removal using non-laser-based approaches. It would also be advantageous to provide methods that enable removal/extraction of the degraded ink components, such as dyes, pigments and other chromophores, from the body to reduce absorption by the body of potentially harmful/toxic chemicals.

It is therefore an object of the present teachings to provide a system and method for removing a tattoo from a subject by exposing ink particles trapped within the dermis to cold plasma.

It is an additional object of the present teachings to provide such a system and method which allows for the extraction of the residue of plasma-treated tattoo ink particles, which may have toxic properties, and of other degradation components from the subject's skin tissues.

It is yet another object of the present teachings to provide methods for removing tattoos which can be performed in one or more treatments and which are effectively less painful to the subject being treated than current conventional methods of tattoo removal.

It is still a further object of the present teachings to provide methods of tattoo removal which can address the limitations of current state-of-the-art removal methods (i.e., laser-based removal systems) to reduce issues with skin scarring, skin color bleaching, and residual tattoo shadowing remaining after removal treatment(s).

SUMMARY

A method and system using cold plasma to remove tattoos from a subject has been developed. In one embodiment, the method for tattoo removal is based on application of a cold plasma which can dislodge and degrade tattoo ink particles trapped within a subject's dermis to facilitate the removal of the mobilized ink particles and/or degradation products thereof from the subject's dermis and surrounding tissues and render the tattoo invisible, non-discernible, and/or undetectable.

In preferred embodiments, the cold plasma is delivered to the subject's dermis via one or more needle or probe-like structures that penetrate the subject's tattooed skin. The cold plasma interacts with constituents present within the dermis such as, but not limited to, the tattoo ink particles themselves, macrophages, fibroblasts, cell membranes, collagen fibers, and capillaries and other cellular and non-cellular constituents of the dermis which have trapped the tattoo ink particles in such a manner as to effectively disrupt the tissue components and dislodge the trapped tattoo ink particles. The cold plasma may also induce degradation of certain types of the ink particles, which are composed of organic and/or inorganic pigments, dyes, and/or chromophores and give color to the ink particles. In preferred embodiments, the cold plasma both dislodges and degrades the trapped ink particles without causing any damage or any significant amount of thermal or other type of irreparable damage to the plasma exposed dermis or other surrounding tissue.

In preferred embodiments, the cold plasma effectively dislodges and degrades all or a portion of the tattoo ink particles during a single or multiple tattoo removal treatment. In some embodiments, multiple treatments may be applied wherein the number of treatments depends on factors such as the size and complexity of the tattoo and on the health of the individual and/or individual's skin. In some embodiments, the dislodged ink particles and degradation by-products thereof can be mobilized to remove them from the subject's dermis and surrounding tissues prior to their recapture by the natural protection mechanisms of the skin, which can otherwise result in a shadowing effect or prior to their transport through the lymphatic channels and deposition in lymph nodes.

In some embodiments, the mobilization step involves the delivery of a pharmaceutically acceptable mobilization fluid which facilitates the removal of the dislodged and degraded ink particles and by-products thereof. The mobilization fluid delivered to the plasma treated dermis is extracted in a subsequent extraction step such as by the application of suction. The extraction of the mobilization fluid containing the dislodged and degraded ink particles from the dermis and surrounding tissues removes the tattoo from the skin.

In preferred embodiments, all or a portion of the dislodged and degraded tattoo ink particles and by-products thereof are extracted from the subject's tattooed dermis during the extraction step. By degrading, dislodging and removing the tattoo ink particles, the tattoo on skin treated according to the method described herein becomes undetectable, invisible, and/or non-discernible to the naked eye. In certain other embodiments, the cold plasma can degrade all or a portion of the tattoo ink particles and the degradation by-products are converted into colorless components and the tattoo becomes undetectable, invisible, and/or non-discernible to the naked eye. In such embodiments, treatment of the tattoo ink particles with cold plasma may render the ink particles down to their colorless atomic, molecular, and/or gaseous components, such as carbon dioxide or water. In some embodiments, the colorless components may not need to be removed or otherwise extracted from the skin if the tattoo has otherwise been rendered undetectable, invisible, and/or non-discernible to the naked eye. In other embodiments, the dislodged and degraded ink particles and degradation by-products thereof which are rendered into colorless components may be absorbed by natural processes from the interstitial fluid of the dermis or elsewhere in the body.

The extraction of the degraded and dislodged ink particles and by-products thereof from the subject's skin is advantageous as the ink particles, components and degradation by-products thereof may have toxic properties which could potentially have harmful effects if absorbed by the subject's body.

In one embodiment, a system for removal of tattoos using cold plasma is formed of (1) cold plasma generation component; (2) optional fluid delivery component; and (3) fluid extraction component. The cold plasma generation component is coupled and connected to a treatment component for delivery of the cold plasma to the tattooed dermis of a subject. The fluid delivery component of the system delivers mobilization fluid to the treatment component which in turn is used to deliver the fluid to the tattooed dermis and surrounding tissue. The mobilization fluid is formed of a pharmaceutically acceptable formulation and facilitates the removal of dislodged and degraded tattoo ink particles and degradation by-products thereof and tissue degradation by-products formed or created during or after exposure to the cold plasma.

The fluid extraction component of the system is coupled and connected to the treatment component to provide suction for extraction of the mobilization fluid and/or removal/extraction of dislodged and degraded tattoo ink particles which may be present in the natural fluids present in the dermis or surrounding tissue directly.

In some embodiments of the system, the cold plasma generation component, fluid delivery component, and a fluid extraction component may be incorporated into a combined free-standing treatment component. In some embodiments, the fluid delivery component may be excluded from the combined treatment component.

In preferred embodiments, the application of a cold plasma, mobilization fluid, and/or extraction (i.e., suction) steps via the treatment component to the tattooed dermis and surrounding tissue is controlled by a skilled/trained operator or technician and the treatment is applied with a high level of precision. In preferred embodiments, all or a portion of the tattoo ink particles are dislodged, degraded, and extracted from the subject's tattooed dermis, to render the tattoo undetectable, invisible, and/or non-discernible to the naked eye.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

Figure 1:
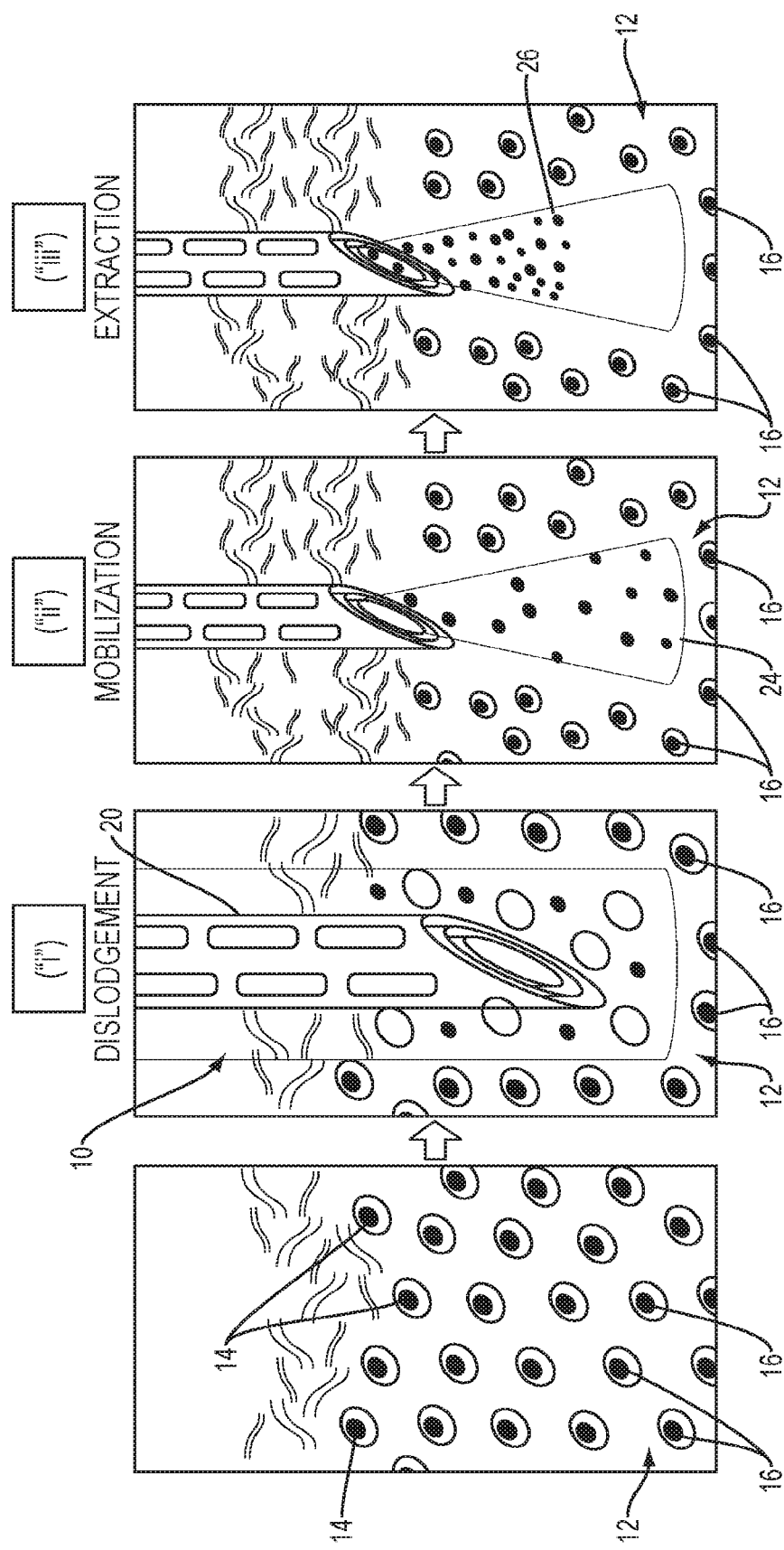
FIG. 1 shows a non-limiting example of a method for tattoo removal including the steps of dislodgement of intra-cellularly trapped tattoo ink particles with a cold plasma, mobilization of the dislodged and degraded ink particles, and extraction of the ink particles for removal of a tattoo from a subject's dermis and surrounding tissue.

Methods and systems for tattoo removal using cold plasma have been developed for the permanent removal of tattoos in a subject's dermis.

I. Definitions

"Cold plasma," as used herein refers to a non-thermal or atmospheric plasma, generated by subjecting a gas(es) to a strong electrical field with a rapidly changing polarity to create a plasma which may contain electrons, highly energetic positively or negatively charged ions, and chemically active species such as ozone, hydroxyl radicals, nitrous oxides and other excited atoms or molecules. In particular, cold or non-thermal plasmas are created at or near standard atmospheric pressure and have temperatures which are close to or near room temperature which are non-damaging when applied to tissue. Contacting tissue with a cold plasma does not increase the tissue temperature at all or significantly, typically only by a few degrees or less.

"Connected," and "coupled," as used herein, refers to directly coupling (i.e., connecting) one element (i.e., output) of a system or component to another element (i.e. input) by any suitable means available, such as, for example, through tubing. Optionally, other intervening elements may also be present.

"Color," as used herein, is broadly defined as a detectable property determined by a substance's electromagnetic absorption and/or emission in the visible spectrum.

"Colorless," as used herein, refers to when essentially no color can be detected apart from the normal coloration of the surroundings (such as skin or other tissue) by the naked eye under normal lighting conditions, for example, diffuse sunlight or standard artificial lighting.

"Dislodged," as used herein, refers to the release of tattoo ink particles from local skin cells and tissue structures such as cells, membranes, and/or tissues, typically found in the dermis.

"Degraded," as used herein, refers to the breakdown of the organic and/or inorganic components of tattoo ink particles due to interaction with an energetic cold plasma via processes that include, but are not limited to, oxidation, reduction, fragmentation, electron decomposition, ion decomposition, or other degradation pathways. Degradation generally refers to a breakdown of a colored organic pigment, dye, or chromophore and/or to the breakdown of the particle size of colored inorganic ink particles which causes them to become colorless. Degradation can come about through the disruption of crystals or amorphous masses of elements such carbon, or by the breaking of chemical bonds in organic or inorganic compounds.

"Pigment, dye, or chromophore," as used herein, are terms that refer to organic and/or inorganic substance(s) which are colored and impart color to a tattoo ink. The color may result from substances which contain heavy metals such as mercury (red), lead (yellow, green, white), cadmium (red, orange, yellow), Chromium (green), cobalt (blue), aluminum (green, violet), titanium (white), copper (blue, green), iron (brown, red, black), barium (white), substances which contain metal oxides such as ferrocyanide and ferricyanide (yellow, red, green, blue), substances such as organic chemicals/compounds such as azo-containing chemicals (orange, brown, yellow, green, violet), naptha-derived chemicals (red), substances such as carbon (i.e., soot or ash) for black ink, and other color compounds which may contain antimony, arsenic, beryllium, calcium, lithium, selenium and sulfur. The pigments, dyes, or chromophores of a tattoo ink are typically dispersed or suspended in a carrier medium which together are delivered to the dermis. The most typical carrier constituents are ethyl alcohol and water, but may be denatured alcohols, methanol, rubbing alcohol, propylene glycol, and/or glycerin.

"Invisible," as used herein, refers to the state of tattoo inks that show essentially no color which can be detected (such as in a tissue) apart from the normal coloration of the surroundings (such as skin or other tissue) by the naked eye under normal lighting conditions, for example, diffuse sunlight or standard artificial lighting.

"Non-discernible and undetectable," are used interchangeably and refer to a substance (i.e., tattoo ink) rendered invisible to the naked eye under normal lighting conditions, and also invisible to the naked eye, or a device, under any other lighting conditions.

"Tattoo," as used herein, refers to a portion of skin, typically the dermis, which has tattoo ink particles embedded or trapped within.

II. Methods of Tattoo Removal

The methods for tattoo removal described herein are based on application of cold plasma to dislodge and degrade tattoo ink particles trapped within a subject's dermis and extraction of the mobilized particles and/or degradation products from the subject's dermis. The method includes the steps of:

(i) dislodging and degrading tattoo ink particles by applying a cold plasma to a subject's tattooed dermis;
(ii) mobilizing the dislodged and degraded ink particles and by-products thereof; and
(iii) extracting the dislodged and degraded ink particles and by-products thereof from the subject's dermis to render the tattoo undetectable, invisible, and/or non-discernible.

In one non-limiting embodiment of the method, as shown in FIG. 1, cold plasma 10 is delivered to the tattooed dermis 12 of a subject and induces dislodgement of ink particles 14 trapped by the cells, membranes, and/or other tissue structures 16 of the dermis 12 which are holding the ink particles 14 in place. The plasma 10 may be delivered by any suitable means known. In preferred embodiments the cold plasma 10 is delivered to the dermis 12 via one or more needle or probe-like structures 20 that can penetrate the subject's tattooed skin. Those skilled in the art will be able to determine the penetration depth of the one of more needle or probe-like structures to deliver the plasma to the tattooed dermis.

It is believed that the cold plasma delivered to a subject's tattooed dermis results in the cold plasma interacting with constituents present within the dermis such as, but not limited to, macrophages, fibroblasts, other cells, collagen fibers, and capillaries which have trapped the tattoo ink particle, in a sufficient amount to effectively disrupt the local dermal skin cells and tissue structures holding the particles and dislodge the trapped tattoo ink particles from the dermis and surrounding tissues. The cold plasma also may induce degradation of the ink particles, which are composed of organic and/or inorganic pigments, dyes, and/or chromophores and give color to the ink particles. Such degradation can result from the interaction of the energetic plasma constituents with the organic and/or inorganic components of the ink particles to degrade them via such processes as oxidation, reduction, fragmentation, electron decomposition, ion decomposition, or other degradation pathways.

In preferred embodiments, the cold plasma both dislodges and degrades the trapped ink particles without causing a significant amount of thermal or other type of irreparable damage to the subject's dermis or surrounding tissue. In some embodiments of the method, the exposure time of the dermis to the cold plasma needed to dislodge and degrade the tattoo ink particles can be as short as one microsecond, but is more preferably a longer period of time, in the range from about one microsecond up to about one hour. In some embodiments, the cold plasma effectively dislodges and degrades the ink particles at the point of plasma exposure within a period of time of 60 minutes or less, more preferably 10 minutes or less. In certain embodiments, the cold plasma may effectively dislodge and degrade all or a portion of the tattoo ink particles within a single tattoo removal treatment. In other embodiments, multiple treatments using cold plasma according to the methods described may be applied. The number of treatments depends on factors such as the area/size and complexity of the tattoo (for example, multi-colored and/or multi-layered tattoo and the age and settling of tattoo inks into lower portion of dermis over time) and on the health of the individual and/or individual's skin. In some non-limiting embodiments, tattooed skin having an area of up to 5 square inches may be treated in as little as one treatment. For tattoos having a larger surface area/size and/or complexity, repeated treatments may be applied with an intervening period time passing between treatments, such as up to one week, up to two weeks, up to three weeks, up to one month, up to two months, or up to three months; longer periods of time may pass between treatments as needed. In preferred embodiments of the method, the temperature of the dermis or other surrounding tissues is not increased by exposure to the cold plasma. In certain other embodiments, the temperature of the dermis or other surrounding tissues when exposed to a plasma treatment is not increased at all or significantly, only increasing by about 1° C. to about 5° C. above normal body temperature, which is below the temperatures needed to induce any significant amount of thermal damage or pain. The application of cold plasma to the dermis for tattoo removal is not expected to produce blanching and/or bleaching of the subject's natural skin color or pigmentation.

Referring to FIG. 1, the dislodged ink particles 14 and degradation by-products thereof are mobilized in a mobilization step to remove them from the subject's dermis and surrounding tissues 12 prior to their recapture by the natural protection mechanisms of the skin, which can result in a re-tattooing effect. In some embodiments, the mobilization step involves the delivery of a pharmaceutically acceptable mobilization fluid 24, preferably through the same one or more needle or probe-like structures used to deliver the cold plasma 22. The mobilization fluid 24 facilitates the removal of the dislodged and degraded ink particles 14 and by-products thereof from the dermis 12. The mobilization fluid delivered to the cold plasma treated dermis is extracted in a subsequent extraction step which can be accomplished by any suitable means, such as by the application of suction. Suction, as used herein, refers to at least a partial vacuum created at the ends of the one or more needle or probe-like structures described above, such that the mobilization fluid containing the dislodged and degraded ink particles 26 is drawn away and extracted from the dermis and surrounding tissues. In some embodiments, suction is applied as a continuous suction or, alternatively, suction can be applied as a non-continuous pulsing suction. In some embodiments, no mobilization fluid is administered during or after the plasma treatment and the dislodged ink particles and degradation by-products thereof are removed by extraction (i.e., suction) of natural bodily fluid(s) containing the particles and by-products from the dermis and/or surrounding tissue during the extraction step.

In preferred embodiments, all or a portion of the dislodged and degraded tattoo ink particles are extracted from a tattoo during the extraction step. By removing dislodged and degraded tattoo ink particles, the tattoo on skin treated according to the method described becomes undetectable, invisible, and/or non-discernible. By definition, an effective amount of cold plasma is applied to cause the colors in the original tattoo in the treated area to become undetectable, invisible and/or non-discernible. In some embodiments, treatment of the tattoo ink particles with cold plasma may render the ink particles down to their colorless atomic, molecular, and/or gaseous components, such as carbon dioxide or water, and the colorless components may not require removal or extraction from the skin if the tattoo has otherwise been rendered undetectable, invisible, and/or non-discernible to the naked eye. In such embodiments, the portion of dislodged and degraded ink particles and degradation by-products thereof which are rendered into colorless components and which remain in the dermis may be absorbed through the interstitial fluid of the body. In such embodiments the method involves dislodging and degrading tattoo ink particles by applying a cold plasma to a subject's tattooed dermis; wherein the cold plasma is applied in an effective amount to a subject's dermis to render the tattoo undetectable, invisible, and/or non-discernible. The application of the steps of mobilizing the dislodged and degraded ink particles and by-products thereof and extracting the dislodged and degraded ink particles and by-products thereof from the subject's dermis as described above are optional and determined at the discretion of the skilled technician or operator applying the tattoo removal method to the subject's tattooed skin. Depending on the extent to which the tattoo has been rendered undetectable, invisible, and/or non-discernible by cold plasma treatment alone the operator/technician may apply steps (ii) and (iii) as shown in FIG. 1 in order to further render the tattoo undetectable, invisible, and/or non-discernible.

In some embodiments, the extraction of the degraded and dislodged ink particles and by-products thereof from the subject's skin is highly desirable as these may have toxic properties. In contrast to laser-based tattoo removal techniques wherein inks and degradation by-products thereof may remain in situ and/or become absorbed by the subject's body, the methods described herein result in extraction of these foreign inks and components in order to prevent their absorption by the subject and any potentially harmful effects on health.

In some embodiments of the method the steps of dislodgement, mobilization, and extraction, as shown in FIG. 1, are performed in sequence as shown, for example, (i) → (ii) → (iii). In embodiments wherein the steps are applied sequentially, the steps are performed so as to provide at least one complete cycle which includes the dislodgement, mobilization, and extraction steps (i), (ii), and (iii). The complete cycle may be repeated any number of times as necessary to effectively remove the tattoo by dislodging and degrading tattoo ink particles from the subject's dermis and tissue. The preferred number of cycles which may be applied are typically in the range of one to 100 cycles, or more. In certain other embodiments, all of the steps are applied concurrently. In a non-limiting example, the dislodgement (application of cold plasma to tattooed dermis), mobilization, which may include the introduction of a mobilization fluid to the dermis, and the extraction step, which involves removal of the mobilization fluid containing the dislodged and degraded ink particles and degradation by-products thereof, or in some instances where no mobilization fluid is used, removes the dislodged and degraded ink particles and degradation by-products thereof directly. In some other embodiments, the steps of dislodgement and mobilization occur concurrently and are followed by the extraction step and form a cycle which is performed at least one or more times, as necessary to remove the tattoo ink from the subject's dermis and rendering the tattoo undetectable, invisible, and/or non-discernible.

In a preferred embodiment of the method described above can further include a pretreatment of the surface of the tattooed skin with an antibiotic solution in order to prevent the introduction of infectious organisms present on the surface to the skin into the dermis during treatment. In other preferred embodiments, the pretreatment may also include application of topical anesthetics to the surface of the skin in order to prevent or alleviate any potential discomfort during the treatment.

1. Cold Plasma

Methods for generating cold plasma as described herein are well-understood by those skilled in the art. Exemplary methods to produce atmospheric cold plasmas include, but are not limited to, are discharge, corona discharge, dielectric barrier discharge (DBD), capacitive discharge, and piezoelectric direct discharge. Typically, such plasmas are generated from a gas or a mixture of gases which include, but are not limited to, air, oxygen, nitrogen, helium, argon, neon, xenon, and krypton. In preferred embodiments, the cold plasma is generated from a mixture of argon and oxygen or a mixture of helium and oxygen. Conditions such as the power, flow rate of gas(es), and the ratio of gases in mixtures used to generate a cold plasma can be optimized as needed to achieve the desired properties of the cold plasma, such as to ensure it is at or near room temperature. In preferred embodiments the power used to generate the plasma is in the range of about 80 W to about 150 W. In some preferred embodiments, the gas flow rates are in the range of about 0.00001 to about 15 L min$^{-1}$. The relative percentages of the one or more gases present in the mixture can be any suitable relative percentage necessary to achieve a cold plasma. In preferred embodiments, wherein the plasma generating mixture of gases is composed of oxygen mixed with argon or helium, the percentage of oxygen in the mixture is preferably in the range of about 0.1% to about 5%.

The cold plasma stream generated according to the methods described herein may be delivered and output into the dermis via one or more needle or probe-like structures as a continuous cold plasma jet stream or can be delivered as a discontinuous pulsed cold plasma jet stream. It should be apparent that the details described herein are non-limiting and that other suitable conditions and parameters can be selected and utilized in order to generate and deliver the cold plasma to the dermis.

2. Pharmaceutically Acceptable Mobilization Fluid

In preferred embodiments, non-limiting examples of the mobilization fluid include sterile water, saline solution, or buffered aqueous solutions. One skilled in the art can readily determine a suitable saline and buffer content and pH for a mobilization fluid/solution to be administered to the dermis of a subject. Representative examples include phosphate buffered saline ("PBS"), Ringer's solution, and sterile physiological saline (0.15 M NaCl).

In certain embodiments, the mobilization fluid can further include surfactants which improve the mobility and removal efficiency of the degraded ink particles and/or degradation by-products thereof. Preferred surfactants include those approved by the U.S. Food and Drug Administration ("FDA") as GRAS ("generally regarded as safe") excipients for injection. In certain other embodiments, the mobilization fluid can also include suitable local anesthetics, anti-infective agents, antiseptic agents, anti-inflammatory agents, and combinations thereof.

Surfactants which can be included in the mobilization fluid may be anionic, cationic, amphoteric, and non-ionic surfactants which are pharmaceutically acceptable for use in a human subject. Anionic surfactants include di-(2 ethylhexyl)sodium sulfosuccinate; non-ionic surfactants include the fatty acids such as butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid, arachidonic acid and esters thereof; surfactants in the amphoteric group include substances classified as simple, conjugated and derived proteins such as the albumins, gelatins, and glycoproteins, and substances contained within the phospholipid classification. Amine salts and quaternary ammonium salts within the cationic group also comprise useful surfactants. Synthetic polymers may also be used as surfactants and include compositions such as polyethylene glycol and polypropylene glycol. Hydrophobic surfactants can be used to improve the removal of hydrophobic ink particles and degradation by-products thereof. Hydrophilic surfactants can be used to improve the removal of hydrophilic ink particles and components and degradation by-products thereof. Amphiphilic surfactants can be used to improve the removal of amphiphilic ink particles and components and degradation by-products thereof.

In some embodiments, anesthetic agents can be included in the mobilization fluid such as local anesthetics, such as but not limited to, -caine anesthetics such as bupivacaine, ropivacaine, dibucaine, procaine, chloroprocaine, prilocaine, mepivacaine, etidocaine, tetracaine, lidocaine, and xylocaine, and mixtures thereof which can be used alone or in combination with other analgesics.

In some embodiments, antiseptic agents can be included in the mobilization fluid. Exemplary antiseptic agents can be composed of any anti-infective compound that prevents the growth of and/or kills infectious organisms. Antiseptic agents are preferably non-irritating and hypoallergenic, such that they do not cause any adverse reactions to the dermis and surrounding tissue of the subject.

"Anti-infective agent," as used herein, refers to common antibacterial, antifungal, and antiviral agents which can be include a chemical substance or group of chemical substances that inhibit the growth of, or destroy microorganisms, fungi, and viruses and are used chiefly in the treatment of infectious diseases. In some preferred embodiments, antibiotics can be included in the mobilization fluid. These may help to prevent infection in the dermis and surrounding tissues of the site of tattoo removal. Exemplary antibiotics include, but are not limited to, chloramphenicol, chlortetracycline, clindamycin, erythromycin, gramicidin, gentamicin, metronidazole, mupiroicin, neomycin, polymyxin B, bacitracin, doxycycline, ampicillin, penicillin, silver sulfadiazine, tetracycline, erythromycin, or combinations thereof.

In some embodiments, anti-inflammatory agents can be included in the mobilization fluid. Anti-inflammatory agents can provide beneficial effects during tissue healing and repair. Anti-inflammatory agents can include, but are not limited to, steroidal anti-inflammatory agents such as dexamethasone, budesonide, beclomethasone, and hydrocortisone and non-steroidal Anti-Inflammatory Agents (NSAIDS). NSAIDS typically inhibit the body's ability to synthesize prostaglandins. Prostaglandins are a family of hormone-like chemicals, some of which are made in response to cell injury. Specific NSAIDS approved for administration to humans include naproxen sodium, diclofenac, sulindac, oxaprozin, diflunisal, aspirin, piroxicam, indomethacin, etodolac, ibuprofen, fenoprofen, ketoprofen, mefenamic acid, nabumetone, tolmetin sodium, and ketorolac tromethamine. Anti-Inflammatory agents are a well-known class of pharmaceutical agents which reduce inflammation by acting on body mechanisms (Stedman's Medical Dictionary 26 ed., Williams and Wilkins, (1995); Physicians' Desk Reference 51 ed., Medical Economics, (1997)).

In some embodiments, the mobilization fluid may further contain additional agents, such as preservatives, viscosity adjusting additives, and other potentially beneficial materials, such as hydrogen peroxide or hemoglobin derived oxygen carriers. Any volume of the formulated mobilization fluid may delivered as needed to the plasma treated dermis in order to effectively facilitate removal of the dislodged and degraded ink particles and by-products thereof during the extraction step. In preferred embodiments the total volume of mobilization fluid used to remove dislodged and degraded ink particles and degradation by-products thereof is less than about 10 mL, more preferably less that about 5 mL, even more preferably less than about 2 mL, and most preferably less than about 1 mL.

III. System for Tattoo Removal

Figure 2:
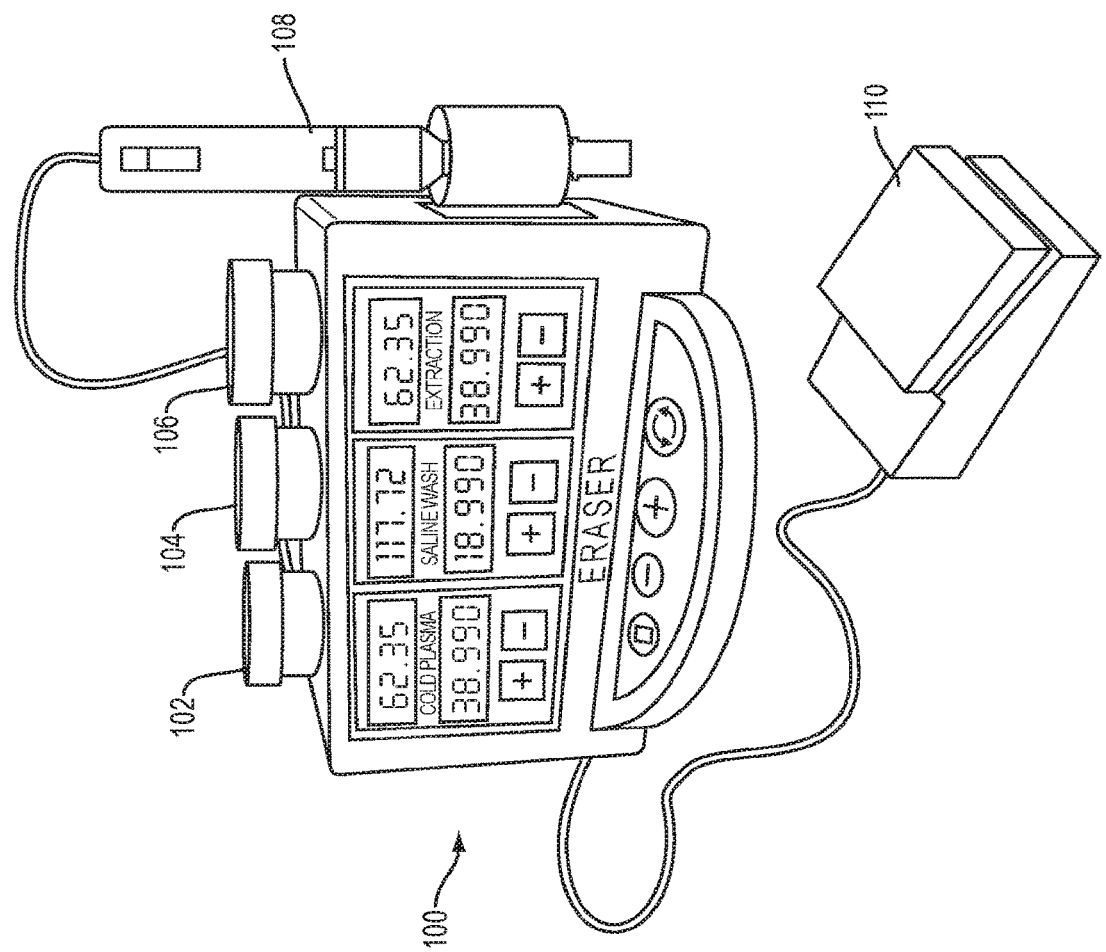
FIG. 2 shows a non-limiting example of the cold plasma-based tattoo removal system.

In one non-limiting embodiment as shown FIG. 2, the system for tattoo removal includes a main housing 100 wherein: a cold plasma generation component 102; a fluid delivery component 104; and a fluid extraction component 106 are integrated. In some other embodiments, the fluid delivery component may be excluded from the system. The system is connected and coupled to a free-standing treatment component 108, which may be in the form of pen or wand-like component. The housing of the tattoo removal system also includes additional components, as needed, to power the aforementioned 102, 104, and 106 components and the treatment component 108, so as to provide power from an electrical outlet or from one or more battery source(s). The main housing may further include one or more control unit(s), which may include input controls (i.e., knobs, buttons, foot pedals) and analog or digital displays which show parameters of the 102, 104, and 106 components in order to control and regulate each component's parameters prior to and during operation. In some embodiments, one (main) control unit may be used to control all the components, while in some other embodiments each component has its own individual control unit on the system's main housing.

In some other embodiments, the cold plasma generation component 102; a fluid delivery component 104; and a fluid extraction component 106 may be incorporated into a single combined treatment component 106. In some embodiments, the fluid delivery component may be excluded from the combined treatment component. A foot pedal 110 can provide means for controlling the cold plasma application, saline wash, and extraction.

It should be understood that a number of modifications could be made to the system and/or components shown in the Figures. For the purposes of clarity, not every component is labeled in every illustration of the system and/or components as shown in the figures, nor is every component of each embodiment shown where illustration is not required to allow one of ordinary skill to understand the system and/or components.

1. Cold Plasma Generation Component

The cold plasma generation component may be built according to specifications for such plasma systems as known in the art. Optionally, the plasma generation unit may be a commercially available component which is adapted to be a part of the tattoo removal system described herein. The plasma generation component housed in the main system includes all necessary components required to generate cold plasma. Components include, but are not limited to, gas inputs, valves, regulators, pumps, gas mixing chamber/units, power systems. The conditions, such as the power, flow rate of gas(es), and the ratio of gases in mixtures used to generate a cold plasma can be controlled as needed to achieve the desired properties of the cold plasma, using the input control(s) connected and coupled to the plasma generation unit.

Typically, plasmas are generated from a gas or a mixture of gases which may include, but are not limited to, air, oxygen, nitrogen, helium, argon, neon, xenon, and krypton. In preferred embodiments, the cold plasma generation unit receives gas(es) from one or more gas sources. In some embodiments, the one or more gas sources may be in the form of free-standing replaceable gas tanks/cylinders or the one or more gas(es) may be from a source such as a gas outlet present on a wall and connected to a central gas source. In certain embodiments, the one or more gas sources are external to the main housing of the tattoo removal system and are coupled and connected to the one or more gas inputs of the plasma generation component of the system by any suitable means (i.e., gas regulator and gas tubing). In certain other embodiments, the one or more gas sources may be included within the housing of the tattoo removal system, if desirable. In preferred embodiments the power used to generate the cold plasma is in the range of about 80 W to about 150 W. In some preferred embodiments, the gas flow rates are in the range of about 0.00001 to about 15 L min$^{-1}$. The relative percentages of the one or more gases present in the mixture can be controlled by a gas mixing unit to achieve any suitable relative gas mix percentage necessary to achieve a cold plasma. In preferred embodiments, wherein the plasma generating mixture of gases is composed of oxygen mixed with argon or helium, the percentage of oxygen in the mixture is preferably in the range of about 0.1% to about 5%.

The plasma generation component is coupled and connected using any suitable means and outputs/delivers the cold plasma generated to the treatment component for delivery to the tattooed dermis. The cold plasma stream generated may be controlled via the one or more input control units of the system. The plasma output by the component to the treatment component may be a continuous cold plasma jet stream or a discontinuous pulsed cold plasma jet stream. It should be apparent that the details described herein are non-limiting and that other suitable conditions and parameters can be selected and utilized in order to generate and deliver the cold plasma to the tattooed dermis. The delivery of cold plasma to the dermis via a treatment component, which may be in the form of a pen/wand, can be controlled by a skilled/trained operator or technician using an input control unit, such as a foot pedal.

In some embodiments, the plasma generation component as discussed above may be incorporated directly into the treatment component. In certain embodiments, the plasma generated in the treatment component is an air plasma and requires no external gas source. In certain other embodiments, one or more gas sources that are external to the treatment component are coupled and connected to one or more gas inputs of the treatment component by any suitable means (i.e., gas regulator and gas tubing). In certain other embodiments, the one or more gas sources may be included within the treatment component, if desirable.

2. Fluid Delivery Component

The fluid delivery component of the system includes one or more fluid reservoir units which can hold a pre-formulated mobilization fluid. The one or more reservoir units are coupled and connected to the treatment component of the tattoo removal system by any suitable means (i.e., tubing) in order to output the mobilization fluid to the treatment component. The mobilization fluid delivery component includes one or more controllable fluid pumps which deliver the mobilization fluid to the treatment component at a controllable flow rate. The flow rate of the fluid can be regulated by the one or more input controls or units coupled and connected to the fluid delivery component. In some embodiments the mobilization fluid is not pre-formulated but can be generated on-demand by mixing units which may form part of the fluid delivery component. Such mixing units are fed by the one or more fluid reservoir units which may contain the component fluids and other agents which form the desired mobilization fluid such as, but not limited to, sterile water, saline solution, buffered aqueous solutions and suitable local anesthetics, anti-infective agents, antiseptic agents, anti-inflammatory agents, and combinations thereof. The delivery of mobilization fluid to the dermis via the treatment component can be controlled by a skilled/trained operator or technician using an input control unit, such as a foot pedal.

In some other embodiments, the fluid delivery component, as described above, may be directly incorporated into a free-standing pen or wand-like component. In such embodiments, one or more disposable fluid cartridges which hold a given volume of pre-formulated mobilization fluid (described above) may be coupled and connected to the fluid delivery component to output the mobilization fluid to one or more needle or probe-like structures of the treatment component as described below. In such embodiments, the delivery of mobilization fluid to the dermis via the one or more needle or probe-like structures of the treatment component can be controlled by a skilled/trained operator or technician using an input control unit present on the treatment component.

3. Fluid Extraction Component

The fluid extraction component of the system includes one or more vacuum pumps and/or other components necessary for creating a vacuum or partial vacuum and is connected and coupled by any suitable means to the treatment component so as to create suction used to extract the mobilization fluid delivered to the dermis during tattoo removal treatment and draw/extract the mobilization fluid containing dislodged and degraded ink particles and by-products thereof, and tissue by-products thereof away from the dermis and surrounding tissues of the subject. In some embodiments of the system which exclude a fluid delivery component and mobilization fluid, the fluid extraction component can remove the dislodged degraded tattoo ink particles which may be present in the natural fluids of the dermis or surrounding tissue directly. In some embodiments, suction created by the extraction component is applied as a continuous suction or, alternatively, the suction can be applied intermittently. The application of suction to the dermis and/or surrounding tissue can be controlled by a skilled/trained operator or technician using an input control unit, such as a foot pedal.

In some other embodiments, the fluid extraction component, as described above, may be directly incorporated into a free-standing pen or wand-like component. In such embodiments, the application of suction to the dermis and/or surrounding tissue can be controlled by a skilled/trained operator or technician using an input control unit present on the treatment component, which may be in the form of a pen or wand.

4. Treatment Component

Figure 3:
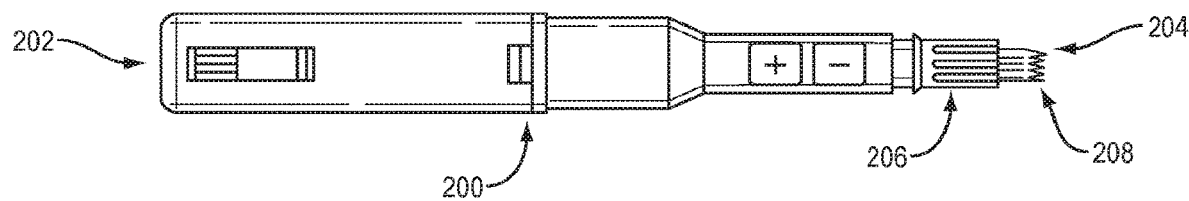
FIG. 3 shows a non-limiting example of a treatment component in the form of a pen or wand which includes a treatment end which contains one or more needle or probe-like structures as part of a disposable cartridge.

The treatment component can be coupled and connected to the components discussed above using any suitable means known. Alternatively, the treatment component can have incorporated into it at least one or more of components as described above. The treatment component is preferably in the form of a pen or wand 200 and is formed of a main body as shown in FIG. 3. The treatment component is also referred to herein as a pen/wand component. The treatment component includes suitable mechanical components, as needed, to deliver cold plasma and mobilization fluid into the dermis and to apply suction to the dermis. One end 202 of the treatment component may include one or more inputs and outputs (not shown) which are connected/coupled to the other components of the system as described above when these components are external to the treatment component. For example, the inputs can receive the cold plasma and mobilization fluid and the output can receive the mobilization or other body fluid extracted from the dermis or surrounding tissue during tattoo removal. The opposite end of the treatment component includes a treatment end which can output and deliver the cold plasma and mobilization fluid into the dermis. The treatment end 204 also receives the mobilization fluid, or other natural body fluids, which contain dislodged and degraded tattoo ink particles during treatment of the dermis and surrounding tissue.

In preferred embodiments, the treatment end 204 is formed of a cartridge unit 206 which contains one or more needle or probe-like structures 208 which penetrate the subject's tattooed skin. The treatment end of the treatment component includes one or more needle or probe-like objects 208 which can penetrate skin and preferably form a part of a removable, disposable, and/or replaceable unit cartridge. The one or more needle or probe-like structures 208 can be made of either plastic, metal or a combination thereof. In some non-limiting embodiments, the removable, disposable, and/or replaceable cartridge includes one, two, three, four, five, six, seven or more needles. The depth of penetration of the one or more needle or probe-like structures, present in the needle cartridge, into the skin is preferably to the depth of the dermis of the subject's tattooed skin but may be adjusted by a skilled/trained operator or technician as needed to apply the tattoo removal treatment method using the system described herein. The one or more needle or probe-like structures 208, which penetrate into the tattooed dermis, oscillate or pulse during tattoo removal treatment via a mechanical process, such as a piston like drive which pulses and/or oscillates the needles in and out of the dermis at varying speeds. In certain other embodiments, the one or more needle or probe-like structures 208, which penetrate into the tattooed dermis are fixed and do not pulse or oscillate.

In some embodiments, the one or more needle or probe-like structures oscillate or pulse and with each oscillation or pulse perform one or more functions of delivering cold plasma to the dermis, delivering mobilization fluid, or extracting the mobilization fluid containing dislodged and degraded ink particles and by-products thereof, and tissue by-products thereof. In some embodiments each full or partial oscillation or pulse applies a particular function sequentially at a time and all the functions as described are performed so as to provide at least one complete cycle which includes the dislodgement, mobilization, and extraction steps. In certain other embodiments, all of the functions are applied concurrently during a given oscillation or pulse of the one or more needles. In some other embodiments, some, but not necessarily all of, the functions described form part of a cycle which is performed at least one or more times during a given oscillation or pulse of the one or more needles, as necessary to remove the tattoo ink from the subject's dermis and rendering the tattoo undetectable, invisible, and/or non-discernible.

As shown in FIG. 3, the one or more needle or probe-like structures 208 which are present at the treatment end 204 of a treatment component in the form of a pen/wand 200 can penetrate into the dermis and deliver cold plasma and deliver and extract fluids to and from the dermis and surrounding tissue undergoing tattoo removal. In some embodiments, different needle/probe-like objects present on the treatment end can serve different functions, such as plasma delivery, fluid delivery, or fluid extraction. In some embodiments, a single needle/probe-like object may perform multiple or all of the aforementioned functions.

Figure 4A:
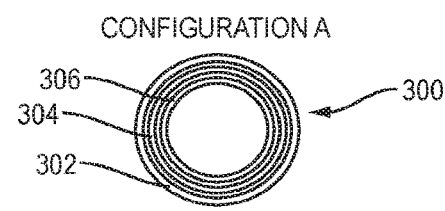
FIGS. 4A and 4B show front (4A) and side (4B) views of a multi-sheathed needle or probe-like structure formed of three concentric nested/embedded needle or probe-like structures forming inner, middle, and outer rings. The outer portion of the needle or probe-like structure includes optional openings.
Figure 4B:
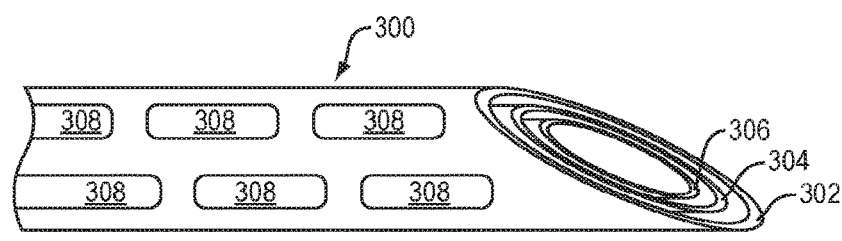

As shown in FIGS. 4A and 4B, each of the needle or probe-like structures of the removable, disposable, and/or replaceable unit cartridge can be formed of a multiple sheathed needle 300 which is formed from nested multiple concentric needles 302, 304, and 306.

In one non-limiting example as shown in the configuration FIGS. 4A and 4B, a multi-sheathed needle or probe-like 300 is formed of three concentric nested/embedded needle or probe-like structures forming inner 306 middle 304, and outer rings 302. In some embodiments, the outer most ring 302 delivers cold plasma and optionally the outer most portion of the needle or probe-like structure includes suitable openings 308 on the outer side for delivering cold plasma to the dermis. In some embodiments, the middle ring 304 delivers mobilization fluid to the dermis. In some embodiments, the inner most ring 302 provides suction to the dermis to remove mobilization fluid containing dislodged and degraded tattoo ink particles and by-products thereof from the dermis.

Figure 5A:
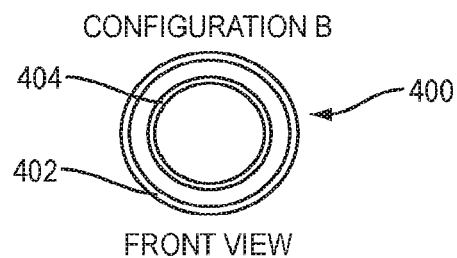
FIGS. 5A and 5B show front (5A) and side (5B) views of a multi-sheathed needle or probe-like structure formed of two concentric nested/embedded needle or probe-like structures forming inner and outer rings. The outer portion of the needle or probe-like structure includes optional openings.
Figure 5B:
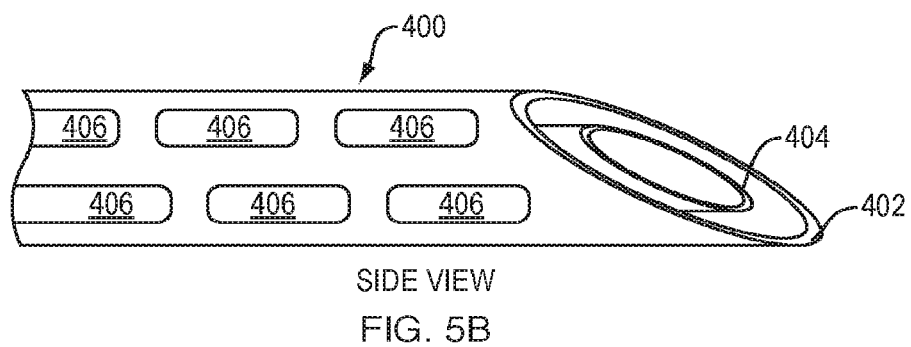

In another non-limiting example as shown in the configuration of FIGS. 5A and 5B, a multi-sheathed needle 400 is formed of two concentric nested/embedded needle or probe-like structures forming inner 404 and outer 402 rings. In some embodiments, the outer most ring delivers cold plasma and extraction fluid which are sequentially pulsed into the dermis. Optionally, the outer most portion 402 of the needle or probe-like structure can include suitable openings 406 on the outer side for delivering cold plasma to the dermis. In some embodiments, the inner ring 404 provides suction to the dermis to remove mobilization fluid containing dislodged and degraded tattoo ink particles and by-products thereof from the dermis.

Figure 6A:
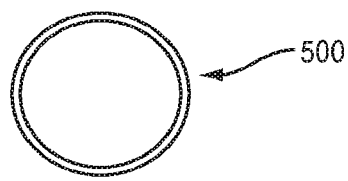
FIGS. 6A and 6B show front (6A) and side (6B) views of a single-sheathed needle. The outer portion of the needle or probe-like structure includes optional openings.
Figure 6B:
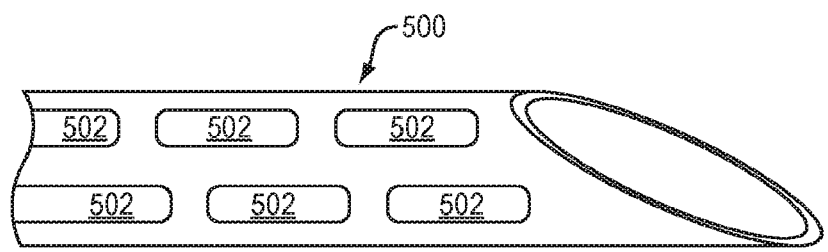

In another non-limiting example as shown in the configuration of FIGS. 6A and 6B, a single-sheathed needle 500 may be used in the cartridge. Optionally, the outer surface of the needle or probe-like structure 500 can include suitable openings 502 on the outer side for delivering cold plasma to the dermis. In a single sheath configuration, the cold plasma, mobilization fluid, and suction are sequentially applied to the dermis during treatment.

As described above, the one or more needle or probe-like structures of the cartridge may each be formed of a multiple sheathed needle-like structure. One of ordinary skill will immediately recognize that the above examples are non-limiting and variations are permitted regarding the use of any of the sheaths present in the embedded/nested structure to achieve any of the plasma, fluid, or extraction functions as described above. In some embodiments, the rate of flow of cold plasma, mobilization fluid and rate of suction can be controlled by a computerized flow meter included in the treatment component.

In some embodiments, an input control, such as a foot pedal or button(s) present on the treatment component, may be used to activate, deactivate, and control all of the cold plasma, dislodgement and mobilization and extraction components coupled and connected to the treatment component, or integrated within the treatment component which may be in the form of a pen/wand, at one time or may control the cold plasma, dislodgement and mobilization and extraction components individually. In some other embodiments, an input control, such as a foot pedal and/or button(s) present on the treatment component, can be used initiate a cycle which triggers each function of a given component in a given sequence (i.e., component 100, then component 102, and subsequently component 104). The cycle/sequence may be repeated at any suitable interval of time and for any suitable number of cycles as needed to remove the tattoo from the subject's dermis and surrounding tissue.

The application of plasma, mobilization fluid, and/or extraction (i.e., suction) through the one or more needle/probe-like structures present on the treatment end to the tattooed dermis and surrounding tissue can be controlled by a skilled/trained operator or technician with high precision. In preferred embodiments, the skilled/trained operator or technician can activate or deactivate the different functions of the system components individually or in combination using one or more input control unit(s), such as a foot pedal or button(s) present on the treatment component. In some embodiments, the operator/technician may apply cold plasma and depending on the extent to which the tattoo has been rendered undetectable, invisible, and/or non-discernible determine not to apply a mobilization fluid and extraction. In certain other embodiments, the operator/technician may choose to further apply a mobilization fluid and extraction in order to further render the tattoo undetectable, invisible, and/or non-discernible. In yet another embodiment, the operator/technician may choose to only further apply extraction to remove dislodged and degraded tattoo ink particles, degradation by-products thereof, and/or tissue by-products thereof contained in bodily fluid without applying a mobilization fluid.

EXAMPLES

Example 1

Removal of Tattoo Ink on Glass Slides

Equipment & Conditions:
An Atomflo™ 500 atmospheric plasma system from Surfx® Technologies with a 1" linear plasma source and a 400×400×300 mm XYZ robot was used in order to evaluate removal of tattoo inks on the surface of a glass slide.

TABLE 1

Cold Plasma Conditions

| | Helium/Oxygen Plasma | Argon/Oxygen Plasma |
|---|---|---|
| Power | 80 W | 150 W |
| Helium Flow Rate | 10 L min$^{-1}$ | 0 |
| Argon Flow Rate | 0 | 15 L min$^{-1}$ |
| Oxygen | 0.4 L min$^{-1}$ | 0.5 L min$^{-1}$ |
| Offset Distance | 2 mm | 3 mm |
| Scan Speed | 20 mm s$^{-1}$ | 10 mm s$^{-1}$ |

Testing:
The argon/oxygen plasma was used to remove tattoo inks (black, red, and yellow) from glass slides at the offset distances and scan speeds given in Table 1. The amount of ink(s) and their concentration(s) in any given area on the slide vastly exceeds the amount(s) and concentration(s) in a human skin tattoo. Each of these inks are representative of classes of molecules used in tattooing. They are, respectively, simple elemental carbon, an organic molecule and an in-organic molecule. These molecular species therefore comprise essentially all of the color components of tattoo inks either used alone or in combinations.

Results:

It was found that application of a cold plasma to a glass slide painted with black, red, or yellow tattoo ink was effective to completely remove the color of the ink and render the slide transparent with only a minimal amount of white residue as evidenced by visual inspection.

Example 2

Removal of Tattoo Ink from Cotton Swabs

Equipment & Conditions:

An Atomflo™ 500 atmospheric plasma system from Surfx® Technologies with a 1" linear plasma source and a 400×400×300 mm XYZ robot was used in order to evaluate removal of tattoo inks on cotton swab tips.

TABLE 2

| | Cold Plasma Conditions | |
|---|---|---|
| | Helium/Oxygen Plasma | Argon/Oxygen Plasma |
| Power | 80 W | 150 W |
| Helium Flow Rate | 10 L min$^{-1}$ | 0 |
| Argon Flow Rate | 0 | 15 L min$^{-1}$ |
| Oxygen | 0.4 L min$^{-1}$ | 0.5 L min$^{-1}$ |
| Offset Distance | 2 mm | 3 mm |

Testing:

The argon/oxygen plasma was used to remove tattoo inks (black, red, and yellow) from cotton swabs at the offset distances given in Table 2. The swabs had been allowed to remain in the solutions/suspensions of inks until the swabs were saturated with ink. The swabs were then allowed to stand for 12 hours before treatment. The amount of ink(s) and their concentration(s) in any given area on the swab vastly exceeds the amount(s) and concentration(s) in an equal volume of tattooed human skin. Each of these inks are representative of classes of molecules used in tattooing. They are, respectively, simple elemental carbon, an organic molecule and an in-organic molecule. These molecular species therefore comprise essentially all of the color components of tattoo inks either used alone or in combinations.

Results:

It was found that application of a cold plasma to a cotton swab painted with black, red, or yellow tattoo ink was effective to remove the color of the ink by visual inspection.

Example 3

Removal of Tattoo Ink from Pig Skin

Equipment & Conditions:

An Atomflo™ 500 atmospheric plasma system from Surfx® Technologies with a 1" linear plasma source and a 400×400×300 mm XYZ robot was used in order to evaluate removal of tattoo inks on the inner and outer surface of pig skin.

An argon/oxygen cold plasma with a temperature of 40° C. was generated using 100 watts of power. The flow rates of argon and oxygen were 15 L min$^{-1}$ and 0.3 L min$^{-1}$, respectively.

Testing:

The argon/oxygen plasma was used to treat the dermal and epidermal sides of pig skin which were painted by black and red tattoo ink and was allowed to remain in place for 12 hours before treatment. The plasma treatment time was 5-10 minutes at an offset distance of 3-4 mm. The amount of ink(s) and their concentration(s) in any given area on the skin vastly exceeds the amount(s) and concentration(s) in an equal volume of tattooed human skin. Each of these inks are representative of classes of molecules used in tattooing. They are, respectively, simple elemental carbon, an organic molecule and an in-organic molecule. These molecular species therefore comprise essentially all of the color components of tattoo inks either used alone or in combinations.

Results:

Visual inspection of the dermal and epidermal sides of the pig skin showed a zone of decoloration of the applied tattoo ink in the treatment area exposed to the cold plasma. Histological preparation of these tissues showed retained tattoo ink in unexposed areas and the absence of such tattoo ink in the exposed areas.

Unless defined otherwise, all technical and scientific terms used herein have the same meanings as commonly understood by one of skill in the art to which the present teachings belong. Publications cited herein and the materials for which they are cited are specifically incorporated by reference.

Those skilled in the art will recognize, or be able to ascertain using no more than routine experimentation, many equivalents to the specific embodiments of the exemplary teachings described herein. Such equivalents are intended to be encompassed by the following claims.

We claim:

1. A system for removing a tattoo from a subject's skin, the system comprising:
   a cold plasma generation component;
   a treatment component integrated with the cold plasma generation component and having a treatment end comprising one or more needle or probe-like structures configured to penetrate the subject's skin to be disposed at a target site for treating a tattooed dermis of the subject; and
   at least one control unit including, a computerized flow meter, configured to control at least one of power and flow rate of a cold plasma generated by the plasma generating component such that a maximum change in temperature of the tattooed dermis that is exposed to the cold plasma remains in a range of about 1° C. to about 5° C.;
   wherein the cold plasma generation component is configured to provide the cold plasma to the treatment end of the treatment component and the treatment component is adapted to deliver the cold plasma via at least one of said one or more needle or probe-like structures to the tattooed dermis of the subject to degrade or dislodge tattoo ink particles without causing thermal damage to the plasma-exposed dermis.

2. The system of claim 1, further comprising a fluid delivery component and an extraction component.

3. The system of claim 2, wherein the fluid delivery component is configured to provide a mobilization fluid to the treatment component and the treatment component is configured to deliver the mobilization fluid to the tattooed dermis of the subject during and/or subsequent to application of the cold plasma.

4. The system of claim 2, wherein the extraction component is configured to provide suction to the treatment component and the treatment component is configured to apply the suction to the tattooed dermis of the subject during and/or subsequent to application of the cold plasma to remove dislodged or degraded ink particles from the tattooed dermis.

5. The system of claim 3, wherein the mobilization fluid comprises sterile water, a saline solution, or a buffered aqueous solution.

6. The system of claim 5, wherein the mobilization fluid further comprises one or more surfactants which improve mobility and removal efficiency of dislodged and degraded ink particles from the dermis or at least one agent selected from local anesthetics, anti-infective agents, antiseptic agents, anti-inflammatory agents, and combinations thereof.

7. The system of claim 6, wherein the treatment component, the fluid delivery component, and the extraction component are integrated into a single housing.

8. The system of claim 7, wherein the fluid delivery component, and the extraction component, are integrated into the treatment component.

9. The system of claim 1, wherein the treatment component is in the form of a pen or a wand.

10. The system of claim 1, wherein the treatment end comprises a cartridge unit which contains said one or more needle or probe-like structures configured to penetrate the subject's tattooed skin.

11. The system of claim 10, wherein the cartridge unit is removable, replaceable, and/or disposable.

12. The system of claim 10, wherein the system further comprises a driver for the one or more needle or probe-like structures configured to induce said structures to oscillate and/or pulse during delivery of said cold plasma to the tattooed dermis.

13. The system of claim 12, wherein the one or more needle or probe-like structures comprises at least one multiple sheathed needle.

14. The system of claim 13 wherein the at least one multiple sheathed needle includes at least one lumen for delivery of cold plasma to the tattooed dermis and at least one additional lumen for delivering a mobilization fluid to the tattooed dermis.

15. The system of claim 13 wherein the at least one multiple sheathed needle includes at least one lumen for delivery of cold plasma to the tattooed dermis and at least one additional lumen for extracting fluid from the tattooed dermis.

16. The system of claim 1, further comprising an extraction component for extracting dislodged or degraded tattoo ink particles via suction of a natural bodily fluid containing the dislodged or degraded tattoo ink particles from the tattooed dermis of the subject.

17. The system of claim 1 further comprising a control unit for controlling at least one of: the rate of flow of cold plasma, rate of flow of mobilization fluid and rate of suction.

18. The system of claim 17 wherein the control unit is configured to control the cold plasma to maintain a treatment region in the tattooed dermis exposed to the cold plasma at a temperature below a target temperature.

* * * * *